(12) United States Patent
Mcmahon

(10) Patent No.: US 8,758,305 B2
(45) Date of Patent: Jun. 24, 2014

(54) ONE-WAY VALVE, ESPECIALLY LOW PRESSURE CHECK VALVE FOR USE IN THE MEDICAL TECHNIQUE

(75) Inventor: Sean Mcmahon, Castletroy (IE)

(73) Assignee: Filtertek S.A., Newcastlewest (IE)

( * ) Notice: Subject to any disclaimer, the term of this patent is extended or adjusted under 35 U.S.C. 154(b) by 739 days.

(21) Appl. No.: 12/160,885

(22) PCT Filed: Jan. 29, 2007

(86) PCT No.: PCT/EP2007/000749
§ 371 (c)(1),
(2), (4) Date: Jul. 14, 2008

(87) PCT Pub. No.: WO2007/085488
PCT Pub. Date: Aug. 2, 2007

(65) Prior Publication Data
US 2010/0152680 A1 Jun. 17, 2010

(30) Foreign Application Priority Data
Jan. 30, 2006 (DE) .................... 20 2006 001 474 U

(51) Int. Cl.
*A61M 5/00* (2006.01)

(52) U.S. Cl.
USPC .......................................... 604/247; 137/854

(58) Field of Classification Search
USPC ........... 604/247, 236, 246; 137/859, 852, 854
See application file for complete search history.

(56) References Cited

U.S. PATENT DOCUMENTS

| | | | | |
|---|---|---|---|---|
| 3,010,477 A * | 11/1961 | Graham | .................... | 137/516.25 |
| 3,710,942 A * | 1/1973 | Rosenberg | .................... | 210/136 |
| 3,850,190 A * | 11/1974 | Carlson | ......................... | 137/218 |
| 4,416,445 A * | 11/1983 | Coad | ............................... | 267/35 |
| 5,893,842 A * | 4/1999 | Imbert | ......................... | 604/110 |
| 5,992,462 A | 11/1999 | Atkinson et al. | | |
| 6,044,859 A | 4/2000 | Davis | | |
| 6,089,272 A | 7/2000 | Brand et al. | | |
| 6,390,120 B1 * | 5/2002 | Guala | ....................... | 137/512.15 |

FOREIGN PATENT DOCUMENTS

| | | |
|---|---|---|
| EP | 0934757 | 8/1999 |
| WO | 9523002 | 8/1995 |
| WO | 9839589 | 9/1998 |

OTHER PUBLICATIONS

ISR for PCT/EP2007/000749 dated Jun. 19, 2007.

* cited by examiner

*Primary Examiner* — Aarti B Berdichevsky
*Assistant Examiner* — Laura Schell
(74) *Attorney, Agent, or Firm* — Lowe Hauptman & Ham LLP

(57) ABSTRACT

One-way valve, especially low-pressure check valve, for use in the medical technology, having a housing consisting of an inlet half and an outlet half and having an inlet channel and an outlet channel with a diaphragm being positioned in a pressure space which is contacting an annular valve seat under pre-tension which is opening into the outlet channel. The pressure space is consisting of two pressure chambers. In the direction of flow before the closing mechanism formed by the valve seat and the diaphragm a second valve mechanism is provided which is opening in the same sense with the first closing mechanism at an over-pressure in the entry channel and which is closing at an over-pressure in the exit channel.

14 Claims, 2 Drawing Sheets

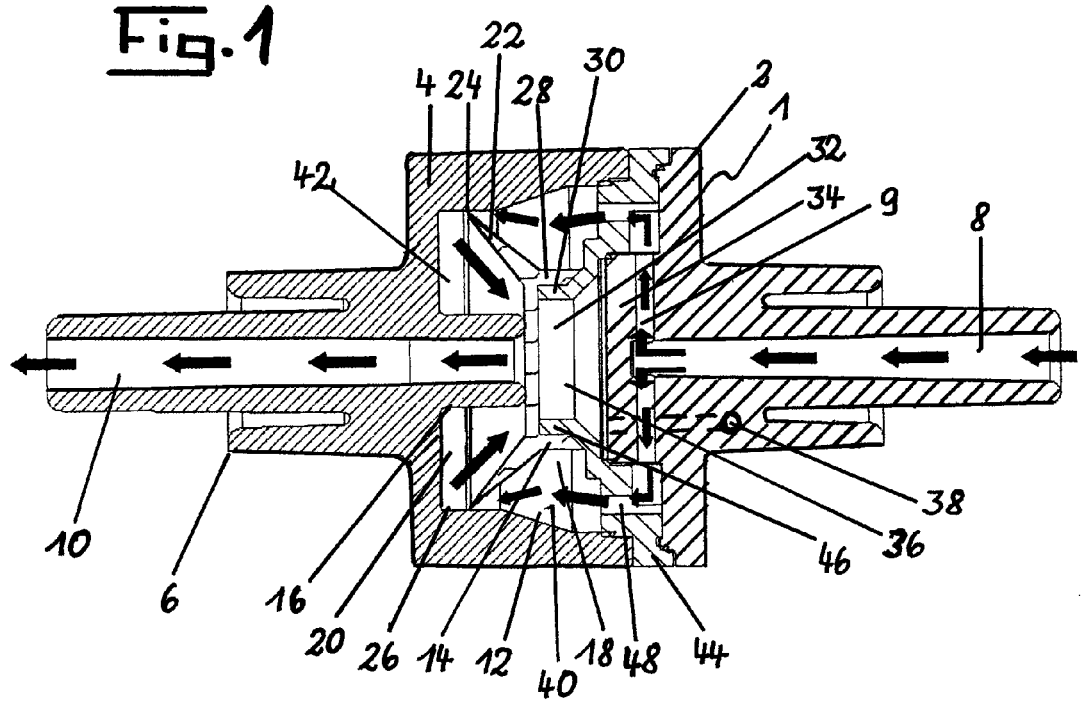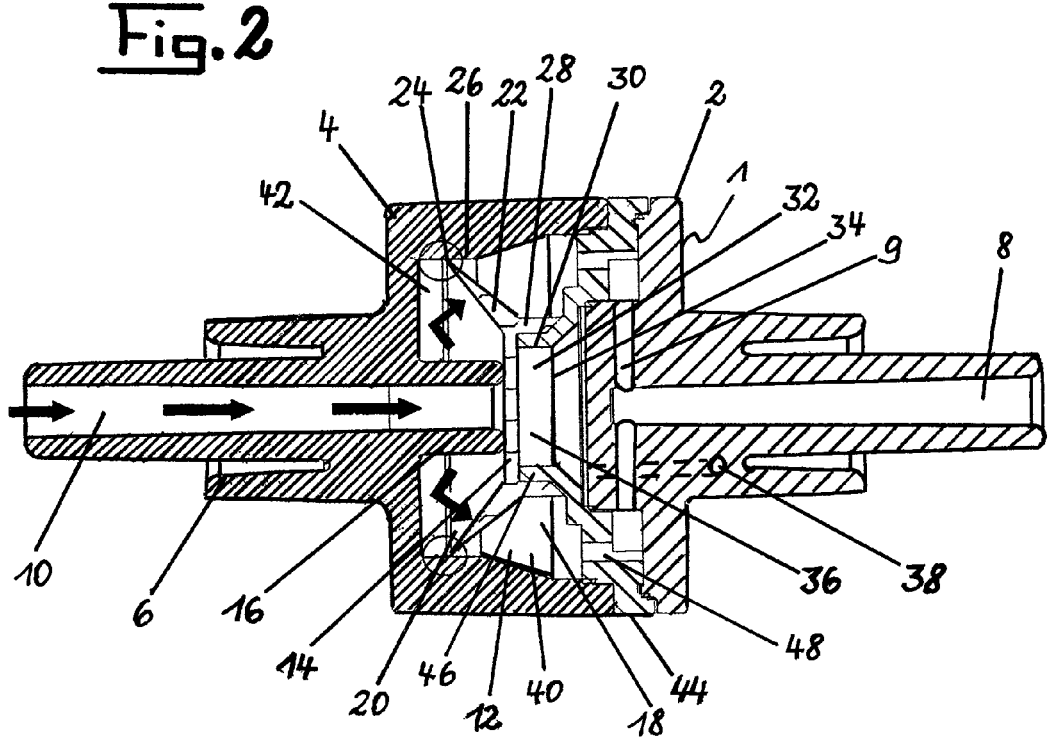

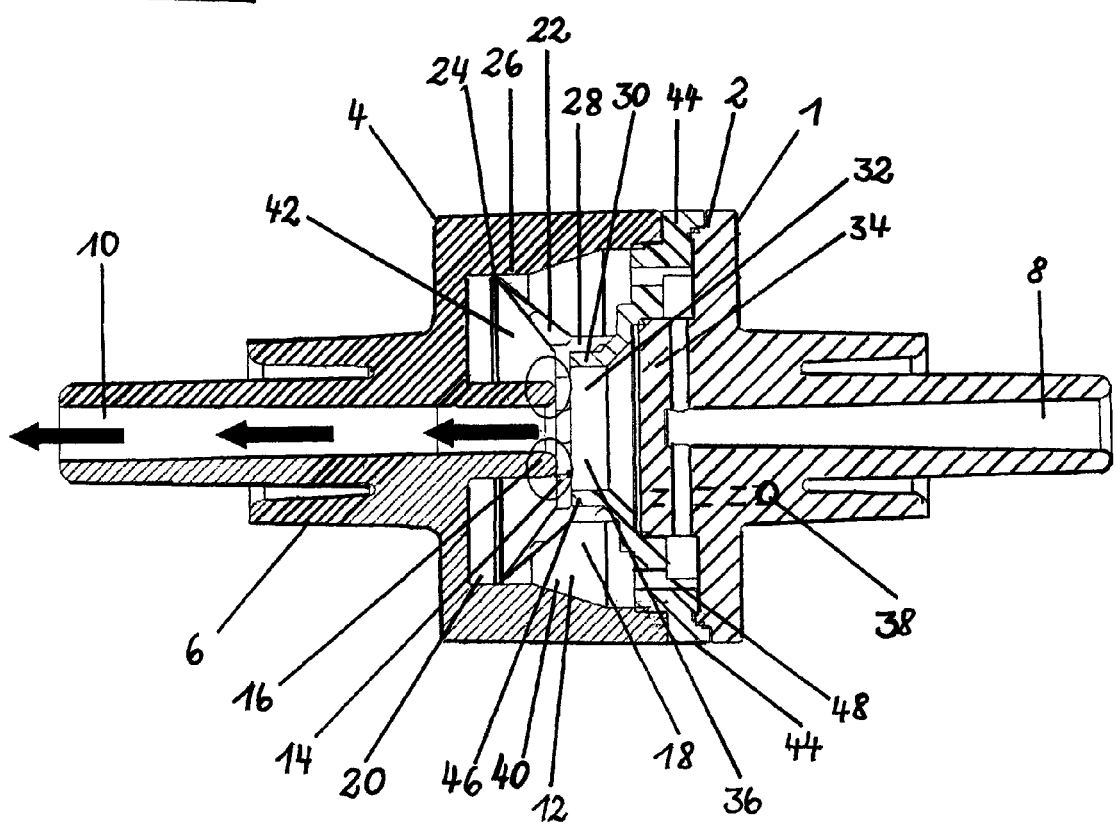

ONE-WAY VALVE, ESPECIALLY LOW PRESSURE CHECK VALVE FOR USE IN THE MEDICAL TECHNIQUE

RELATED APPLICATIONS

The present application is based on International Application Number PCT/EP2007/000749 filed Jan. 29, 2007, and claims priority from German Application Number 20 2006 001 474.8 filed Jan. 30, 2006, the disclosures of which are hereby incorporated by reference herein in their entirety.

BACKGROUND

The invention relates to a one-way valve, especially a low pressure check valve, for use in the medical technique, having a housing consisting of an inlet half and an outlet half, which is provided with an inlet channel and an outlet channel and having a diaphragm provided in a pressure space which is contacting an annular valve seat under pretension leading to the outlet channel, wherein the pressure space is consisting of two pressure chambers.

One-way valves of this kind are used as stop valves against complete emptying, especially in infusion sets, wherein such valves are used to prevent the ingress of air into the infusion fluid during the empting of a reservoir being filled with the infusion fluid by providing for an instant stop of the flow such that towards the end of the feed no air can get into the venous system of a patient via the lines connected to the venous system.

A check valve for the use in an infusion set for example is known from the DE 2919343 A1 which is having a drip chamber and a float valve which is preventing the ingress of air into the infusion line during the empting of the chamber. On the exit side in the flexible hose line leading to the infusion needle there is provided a roller clamp. To prevent the entire line system of the infusion set from filling with air a double-seat float valve is used having a ball as a float, wherein however such ball float valves are not acting sufficiety exact such that an ingress of air into the infusion hose cannot prevented in any case.

From the DE 3632412 A1 further a drain-off safety device is known in which in the direction of flow ahead the drip chamber a valve acting at drain-off is positioned. In this valve a float ball under friction is contacting a channel wall when sealing and cannot prevent an admission of air with absolute safety. The two above-mentioned valves are not suitable to safely exclude the admission of air into the human venous system.

From the DE 19749562 A1 further an infusion set is known which is consisting of a highly suspended container for the infusion liquid and a drip chamber which is connectable by a tubular spike to a flow restrictor container as well of a roller clamp being adjustable on a flexible line below the container and an injection needle at the distal end of the line. In the direction of flow before the drip chamber or at the entrance thereof there is provided an empty drain stop to prevent the ingress of the air into the infusion liquid especially toward the end of the feed of the infusion liquid. By means of the drain empty stop or the valve provided therein, respectively, depending from an existing static pressure the flow of the infusion liquid can be switched off. In the practical use however it has been found that the anti-drain stop which is working in dependence from the existing static pressure of the infusion liquid is not sufficient to safely prevent the entrance of air. Especially if the possibility is given that the connections are exchanged by negligence and followingly the function of the anti-drain stop valve is not ensured anymore an especially dangerous situation is given when due to this air can reach the infusion system which could lead to an embolism of the patent if such air reaches the venous system. It is therefore essential that no air can be taken along with the infusion liquid. An especial disadvantage of the valve of this design is consisting in the fact that when a static over-pressure is existing on the exit side then there is no possibility to prevent the ingress of air into the system.

A comparatively complex safety valve for infusions is known from the WO 97/03712 A2 by the means of which it should be prevented that blood from the vein is flowing out in case infusion lines unintentional are separated.

From the DE 19643360 C1 further a three-way diaphragm valve is known which between a valve housing and a diaphragm, on the one side, and a cover at the diaphragm, on the other side, is having separate differential pressure chambers of which the differential pressure chamber on the side of the valve housing is having a first connection for the inlet line, the cover having a second connection for the inlet line and, the differential pressure chambers having a connection for the outlet line.

A one-way valve of the above-defined kind is known according to a prior proposal of the applicant from the DE 10219994 in which the two pressure chambers are positioned side-by-side and connected by means with a connection channel. The diaphragm is extending either as two separate parts or as one unitary part through both pressure chambers, wherein the diaphragm in the first pressure chamber is contacting a first valve seat being positioned in an pre-chamber under tension and is having a central opening being closed by the first valve seat. A further opposedly directed annular valve seat leading to the outlet channel is provided in the sec- and pressure chamber, wherein on the side of the diaphragm opposite to the valve seat a second pre-chamber is provided being connected to atmosphere. By means of this known valve the ingress of air into the system of the infusion set safely is prevented as well at an existing static negative pressure as the existence of an over-pressure in the exit channel. A static negative pressure in the inlet channel for example can occur if a reservoir of the infusion liquid has run dry, if an infusion pump is working incorrectly or if air has gotten into the system. In this case the check valve in the first pressure chamber is safely closing. An over-pressure in the exit channel for example can occur during a temporary closure of the brachial vein of a patient if on the exit side additionally a medicine pump is connected. An over-pressure here would lead to the fact that the drug is pumped into the infusion set working with gravity. This known one-way valve is comparatively complex with respect to the production thereof and has a comparatively large space requirement due to the pressure chambers being arranged side-by-side.

SUMMARY

It is therefore the task to be solved by the present invention to propose a room-saving construction of such a valve which can be produced under less expenditure while maintaining the advantages achieved by the known valve.

In a one-way valve of the above-defined kind this task basically is solved by the features that a second valve mechanism is provided in the direction of flow ahead of the closing mechanism formed by the valve seat and that the diaphragm which at an over-pressure in the entry channel is opening in the same sense with the first closing mechanism and which at an over-pressure in the outlet channel is closing.

An especially preferred embodiment according to the invention in this connection is created by the features that the second valve mechanism is formed by an annular cup-like skirt formed at the radially outer margin of the diaphragm which in the opening direction is angularly directed upwardly and which at its free outer edge is contacting the interior wall of the pressure space under pre-tension and which is separating the pressure chambers from each other.

It is obvious that the means of one and the same of the diaphragm both functions within an infusion set are ensured such that due to the fact that simultaneously the interior wall of the housing is used as a valve seat a very compact and concentric design can be achieved which essentially is using fewer space. Simultaneously it is ensured that in both abovementioned cases a further transport of the infusion fluid reliably is ended and therefore an entering of infusion liquid containing air into the veins is prevented. Simultaneously by the one-way valve it is ensured that with an over-pressure existing on the exit side caused by an infusion or medicine pump the valve is closing due to the fact that the second valve mechanism formed by the annular cup-like skirt at the radially outer margin of the diaphragm which then is contacting the inner wall of the housing is closing and therefore a medicine cannot reach the infusion set in spite of the fact that in this case the closing mechanism leading to the exit channel would open. A possible temporary over-dosing therefore safely is prevented.

An advantageous improvement of the invention can be achieved by the feature that the diaphragm on the side opposite to the cup-like skirt is having an annular wall directed downwardly which is overlapping an annular supporting wall of the housing. This forms an especially simple form of support and mounting of the diaphragm due to the fact that the margin thereof in the shape of the cup-shaped skirt is used as a closing member which means that for the mounting a clamping of the diaphragm is not possible anymore.

In detail it is of advantage that the space enclosed by the supporting wall is closed by a housing wall opposite to the valve seat, whereby a pre-chamber opposite to the valve seat is formed and that the pre-chamber is connected to atmospheric pressure by an opening in the housing. By these features it is achieved that the construction of the valve becomes extremely compact by using the space formed by the support of the diaphragm on the supporting wall is used as an pre-chamber, wherein the admission of atmospheric pressure is ensuring a quick reaction of the diaphragm with respect to the valve seat leading to the exit channel.

In detail it is further of advantage that the inlet channel is connected with a first annular space which is limited by the supporting wall or the over-lapping annular wall, respectively, and that the cup-shaped skirt in the exit half and is forming the first pressure chamber. By this feature due to the concentric construction further the room requirement is reduced.

An especially preferred embodiment according to the invention can be created by the features that a second annular space is surrounding the valve seat which is separated from the first annular space by the cup-shaped skirt and which is forming the second pressure chamber.

In detail it is preferred to perform the supporting wall monolithic with a member positioned between the inlet half and the outlet half. These features are serving the purpose to reduce the costs for the production of the valve members usually manufactured by injection molding since thereby the members can be produced with simpler molds.

In this connection it is preferred that the member is forming the radial outer wall of the pre-chamber and is having connection channels beyond the pre-chamber which are connecting the inlet channel with the first pressure chamber. In this way simply the pre-chamber opposite to the valve seat can be produced.

To ensure a safe sealing and fast working an advantageous feature is consisting in the fact that the cross-section of the skirt is radially decreasing to its outer margin and therefore is ending in a sharp edge contacting the interior wall of the housing.

BRIEF DESCRIPTION OF THE DRAWINGS

In the following, the invention is more detailly described with reference to an exemplary embodiment shown in the drawings. In the drawings show:

FIG. 1 a schematic sectional view of a one-way valve according to the invention in the state of normal flow during an infusion;

FIG. 2 a sectional view corresponding to FIG. 1 in a state in which a back-flow through the valve is prevented when an over-pressure in the outlet is existing and, FIG. 3 a sectional view corresponding FIGS. 1 and 2 in a state in which the flow is prevented in the case that a negative pressure is existing in the exit.

DETAILED DESCRIPTION

The embodiment of the one-way valve 1 according to the invention shown in the drawings in different possible operational states which is a low pressure check valve to be used in the medical technology, especially in connection with infusions, is having an inlet half 2 consisting of plastics and being produced by injection molding and an outlet half 4 manufactured the same way forming together a housing 6. The inlet half 2 is containing an inlet channel 8 which is in the intended field of use is connected to a container (not shown) containing the infusion liquid or an infusion pump not shown either. The outlet half 4 is containing an outlet channel 10 which by means of a hose not shown with a roller clamp is leading to an infusion needle. In a pressure space 12 formed in the housing 6 a diaphragm generally designated with 14 consisting of an elastic material like silicon or a thermoplastic elastomere is positioned. The diaphragm 14 under pre-tension is engaging a valve seat 16 projecting into the pressure space, the valve seat 16 surrounding the outlet channel 10 is connected with the same.

The pressure space 12 is consisting of two pressure chambers 18 and 20 separated from each other by the diaphragm 14.

According to the invention in the direction of flow which would prevailing in the normal state as shown by the arrows in FIG. 1 ahead of the closing mechanism formed by the valve seat 16 and the diaphragm 14 a further valve mechanism is provided which with an existing over-pressure in the entry channel 8 in the same sense is opening together with a first valve mechanism 14, 16 and which with an over-pressure in the exit channel 10 is closing in case such over-pressure should lift the diaphragm 14 from the valve seat 16.

In the preferred embodiment shown in the drawings the second valve mechanism is formed by an annular cup-shaped skirt 22 which in the flow direction shown in FIG. 1 is directed angular upwardly. The cup-shaped skirt 22 is unitary with the diaphragm 14, wherein the skirt 22 is decreasing in section radially to the exterior and is ending in an annular sharp outer edge 24. The outer edge 24 is contacting the interior wall 26 of the pressure space under pre-tension due to the elasticity of the skirt 22 such that the interior wall 26 so to say is forming the valve seat of the second valve mechanism which can be opened and closed by the cup-shaped skirt 22. The skirt 22 together with the interior wall 26 is separating the pressure chambers 18 and 20 from another.

On the side opposite to the cup-shaped skirt 22, the diaphragm 14 has a unitary annular wall 28 projecting downwardly, which is covering an annular supporting wall 30 at the housing 6. By this kind of support, a simple mounting is possible by merely pushing the diaphragm 14 with its annular wall 28 over the annular supporting wall 30, which generally forms part of the inlet housing 2. Simultaneously, this leads to the advantage that the valve seat 16, as well as the interior wall 26 forming the valve seat for the outer edge 24 of the cup-shaped skirt 22, are deeply positioned within the exit housing 4 such that these parts are protected against any damage during manufacture and assembly, especially during injection from the injection molding mold.

As shown, the space 32 surrounded by the supporting wall 30 is closed by a housing wall 34 which is positioned opposite to the valve seat 16. The space closed by the supporting wall 30 and the housing wall 34 is forming a pre-chamber 36 being positioned opposite to the valve seat 16. The pre-chamber 36 is connected to the atmosphere by a housing opening 38 shown in the drawings in dotted lines such that the pre-chamber 36 is exposed to atmospheric pressure. By this feature it is achieved that during the opening of the first closing means, i.e. during the lifting of the diaphragm 14 from the valve seat 16, no counter-pressure can form such that the diaphragm 14 in minimal times and easily can open and close.

The entry channel 8 by means of radial channels 9 being provided within the entry housing 2 is connected to a first annular space 40 which is delimited by the supporting wall 30 or the covering annular wall 28 of the diaphragm 14 and the cup-shaped skirt 22 and is positioned within the exit housing 4 such that the outer limit of the first annular space 40 is formed by the wall of the exit housing 4. The first annular space 40 is forming the first pressure chamber 18.

A second annular space 42 is surrounding the valve seat 16 and is separated from the first annular space 40 by the cup-shaped skirt 22 and is forming the second pressure chamber 20.

As shown for reasons of manufacture, it is preferred to make the supporting wall 30 unitary with a member 44 positioned between the inlet housing 2 and the outlet housing 4, wherein the member 44 forms the radially exterior wall 46 of the pre-chamber 36 and provides connection channels 48, which are connecting the radial channels 9 leading to the entry channel 8 with the first pressure chamber 18 exterior to pre-chamber 36.

The member 44 is overlapping the housing wall 34 and is joined with the walls of the inlet housing 2 and outlet housing 4, e.g. by ultrasonic welding.

In the following, the different kinds of function of the embodiment of the one-way valve according to the invention shown in the drawings, wherein the different states in the different figures are indicated by black arrows.

FIG. 1 is showing the normal state of flow during an infusion in which the infusion liquid is entering the entry channel 8 and after passing the valve section is leaving from the exit channel 10 after the opening pressure of the valve had been reached by a corresponding increase of pressure in the entry channel 8. In this state the infusion liquid is flowing from the inlet channel 8 via the radial channels 9 and the connection channels 48 into the first pressure chamber 18 formed by the annular space 40, is lifting the outer edge 24 of the skirt 22 from the interior wall 26 of the pressure space 12 and is flowing around the outer edge 24 and is reaching the second pressure chamber 20. Here the centre area of the diaphragm 14 is lifted from the valve seat 16 such that the flow continues into the exit channel 10.

FIG. 2 is showing the state in which in the inlet channel there is no pressure and in which by a still existing pressure in the outlet channel a flow-back would be possible. The infusion liquids in this state tries to flow back through the outlet channel 10 and lifts in this state the centre area 14 from the valve seat 16. In this state however in the second pressure chamber 20 the outer edge 24 of the cup-shaped skirt 22 is pressed against the interior wall 26 such that a flow-back is prevented.

In the state shown in FIG. 3 the functioning of the one-way valve according to the invention is shown to prevent the flow in case negative pressure is existing in the outlet channel. In this case the centre area of the diaphragm 14 fixedly is pressed against the valve seat 16 such that here, too, no unintended flow is possible. It is obvious that all possible operative states are considered in a safe and advantageous way.

One advantage of the construction design additionally is residing in the fact that the entry channel 8 and the outlet channel 10 are axially aligned such that an extremely compact construction is achieved. Further it is of advantage that all sealing areas are protected against damage during the manufacture, the transport and the assembly. The one-way valve according to the invention does not switch off in case at the entry an over-pressure is present.

In spite of the fact that in the drawings the one-way valve according to the invention merely is shown with hose connectors, it is obvious that these connectors easily could be changed to provide for exampler Luer-lock connectors or similar connectors on both sides of the valve.

All features and advantages of the invention which can be learned from the specification, the claims and the drawings including constructive details and positions in space could be essential for the invention both individually and in deliberate combination.

The invention claimed is:

1. A low-pressure check valve for use in medical technology comprising:
   a housing comprising an inlet half and an outlet half, wherein the housing includes an inlet channel and an outlet channel;
   an annular valve seat formed in the outlet half and opening into the outlet channel;
   a pressure space comprising a first pressure chamber and a second pressure chamber;
   a diaphragm, wherein the diaphragm is contacting the annular valve seat and is under tension, and wherein the diaphragm overlaps an annular supporting wall of the housing upstream to an annular cup-shaped skirt;
   a first valve mechanism formed by the annular valve seat and the diaphragm; and
   a second valve mechanism, wherein the second valve mechanism is formed by the annular cup-shaped skirt formed at an outer radial margin of the diaphragm; has a free outer edge contacting an interior wall of the housing; and separates the pressure chambers from each other,
   wherein the second valve mechanism
      opens at an over-pressure in the first pressure chamber; and
      closes at an over-pressure in the second pressure chamber.

2. The check valve according to claim 1, wherein a space enclosed by the annular supporting wall is enclosed by a housing wall opposite to the annular valve seat, whereby a pre-chamber opposite to the annular valve seat is formed by the annular supporting wall and the housing wall, and the pre-chamber is connected to atmospheric pressure by an opening in a wall of the housing.

3. The check valve according to claim 1, wherein the inlet channel is connected with the first pressure chamber, and wherein the first pressure chamber is formed by the supporting wall of the housing or an overlapping annular wall of the diaphragm, the interior wall of the housing, and the annular cup-shaped skirt.

4. The check valve according to claim 3, wherein the second pressure chamber is formed by the annular valve seat, the interior wall of the housing, and the annular cup-shaped skirt.

5. The check valve according to claim 1, wherein the supporting wall of the housing is a part of a monolithic member positioned between the inlet half and the outlet half.

6. The check valve according to claim 5, wherein the monolithic member forms the radial outer wall of a pre-chamber and has connection channels exterior to the pre-chamber, wherein the connection channels connect the inlet channel with the first pressure chamber.

7. The check valve according to claim 1, wherein a cross-section of the cup-shaped skirt decreases in thickness to its outer margin.

8. A low-pressure check valve for use in medical technology comprising:
   a housing comprising an inlet half and an outlet half, wherein the housing includes an inlet channel and an outlet channel;
   a valve seat formed in the outlet half and opening into the outlet channel;
   a pressure space comprising a first pressure chamber and a second pressure chamber;
   a diaphragm, wherein the diaphragm is contacting the valve seat and is under tension, and wherein the diaphragm overlaps an annular supporting wall of the housing upstream to an annular cup-shaped skirt;
   a first valve mechanism formed by the valve seat and the diaphragm; and
   a second valve mechanism, wherein the second valve mechanism is formed by the annular cup-shaped skirt formed at an outer radial margin of the diaphragm; has a free outer edge contacting an interior wall of the housing; and separates the pressure chambers from each other,
   wherein the second valve mechanism
      opens at an over-pressure in the first pressure chamber; and
      closes at an over-pressure in the second pressure chamber.

9. The check valve according to claim 8, wherein a space enclosed by the annular supporting wall is enclosed by a housing wall opposite to the valve seat, whereby a pre-chamber opposite to the valve seat is formed by the annular supporting wall and the housing wall, and the pre-chamber is connected to atmospheric pressure by an opening in the housing wall.

10. The check valve according to claim 8, wherein the inlet channel is connected with the first pressure chamber, and wherein the first pressure chamber is formed by the supporting wall of the housing or an overlapping annular wall of the diaphragm, the interior wall of the housing, and the annular cup-shaped skirt.

11. The check valve according to claim 10, wherein the second pressure chamber is formed by the valve seat, the interior wall of the housing, and the annular cup-shaped skirt.

12. The check valve according to claim 10, wherein the supporting wall of the housing is a part of a monolithic member positioned between the inlet half and the outlet half.

13. The check valve according to claim 12, wherein the monolithic member forms the radial outer wall of a pre-chamber and has connection channels exterior to the pre-chamber, wherein the connection channels connect the inlet channel with the first pressure chamber.

14. The check valve according to claim 8, wherein a cross-section of the cup-shaped skirt decreases in thickness to its outer margin.

* * * * *